US00PP33092P2

(12) United States Plant Patent
Ronald

(10) Patent No.: US PP33,092 P2
(45) Date of Patent: May 25, 2021

(54) ***PHYSOCARPUS* PLANT NAMED 'JEFROY'**

(50) Latin Name: *Physocarpus opulifolius*
Varietal Denomination: Jefroy

(71) Applicant: Jeffries Nurseries Ltd, Portage la Prairie (CA)

(72) Inventor: Wilbert Ronald, Portage la Prairie (CA)

(73) Assignee: JEFFRIES NURSERIES LTD, Portage la Prairie (CA)

( * ) Notice: Subject to any disclaimer, the term of this patent is extended or adjusted under 35 U.S.C. 154(b) by 0 days.

(21) Appl. No.: 16/873,310

(22) Filed: Mar. 18, 2020

(51) Int. Cl.
*A01H 5/12* (2018.01)
*A01H 6/74* (2018.01)

(52) U.S. Cl.
USPC ..... Plt./226

(58) Field of Classification Search
USPC ..... Plt./226
CPC ... A01H 5/02; A01H 5/00; A01H 5/12; A01H 6/74; A01H 6/00
See application file for complete search history.

(56) References Cited

U.S. PATENT DOCUMENTS

PP30,820 P2 * 8/2019 Verhoef ..... A01H 6/74
Plt./226

OTHER PUBLICATIONS

Green Haven Garden Centre 2018 Price List, retrieved on Aug. 24, 2020, retrieved from the Internet at https://www.greenhavengarden.ca/assets/files/2018%20Catalog_WEB.pdf, cover page, 2 introductory pages, p. 18. (Year: 2018).*

Issuu Northern Garden Collection 2018 published 2017, retrieved on Aug. 24, 2020, retrieved from the Internet at https://issuu.com/psrpsr/docs/ngc_2018-, cover page, pp. 2, 28. (Year: 2017).*

* cited by examiner

*Primary Examiner* — June Hwu
(74) *Attorney, Agent, or Firm* — Penny J. Aguirre

(57) ABSTRACT

A new cultivar of *Physocarpus* plant named 'Jefroy' that is characterized by its foliage that is dark purple in color with the color retained throughout the summer, its compact, dwarf plant habit with tidy branching, its leaves that are similar in size to *Physocarpus* cultivars that lack a dwarf plant habit, and its good resistance to powdery mildew.

2 Drawing Sheets

Genus/species: *Physocarpus opulifolius.*
Varietal denomination: 'Jefroy'.

BACKGROUND OF THE INVENTION

The present invention relates to a new and distinct cultivar of *Physocarpus opulifolius* and will be referred to hereafter by its cultivar name, 'Jefroy'. 'Jefroy' represents a new cultivar of *Physocarpus*, a deciduous shrub grown for landscape use.

The new *Physocarpus* arose from a breeding program conducted by the Inventor in Portage la Prairie, Manitoba, Canada. The objective of the breeding program was to develop new *Physocarpus* cultivars with unique foliage color combined with compact plant habits and disease resistance.

The new *Physocarpus* originated from open pollination in summer of 2007 of *Physocarpus* cultivars 'Monlo' (U.S. Plant Pat. No. 11,211), 'Seward' (U.S. Plant Pat. No. 14,821), and 'Center Glow' (U.S. Plant Pat. No. 16,894) and the seeds were pooled and sown. The new cultivar 'Jefroy' was selected as a unique single plant from the resulting seedlings in summer of 2011.

Asexual propagation of the new cultivar was first accomplished by stem cuttings by the Inventor in June of 2012 in Portage la Prairie, Manitoba, Canada. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new *Physocarpus*. These attributes in combination distinguish 'Jefroy' as a unique and distinct cultivar of *Physocarpus*.

1. 'Jefroy' exhibits foliage that is dark purple in color with the color retained throughout the summer.
2. 'Jefroy' exhibits a compact, dwarf plant habit with tidy branching.
3. 'Jefroy' exhibits leaves that are similar in size to *Physocarpus* cultivars that lack a dwarf plant habit.
4. 'Jefroy' exhibits good resistance to powdery mildew.

The possible female parent plants of 'Jefroy' all differ from 'Jefroy' in having less compact plant habits, taller plant heights, and in having lighter and different foliage coloration. 'Jefroy' can be most closely compared to *Physocarpus opulifolius* cultivars 'SMPOTW' (U.S. Plant Pat. No. 26,749), 'SMNPOTWG' (U.S. Plant Pat. No. 28,857), and 'N5' (U.S. Plant Pat. No. 30,820). 'SMPOTW' and 'SMNPOTWG' are similar to 'Jefroy' in having a dwarf plant habit and flowers that are pink-white in color. 'SMPOTW' differs from 'Jefroy' in having foliage that is bronze-maroon in color and leaves that are smaller in size. 'SMNPOTWG' differs from 'Jefroy' in having foliage that is golden in color and leaves that are smaller in size. 'N5' is similar to 'Jefroy' in having dark foliage and a compact plant habit. 'N5' differs from 'Jefroy' in having foliage that is wider and more black in color that develops a red coloration in fall and in having a slightly more mounded plant habit.

BRIEF DESCRIPTION OF THE DRAWINGS

The accompanying colored photographs illustrate the overall appearance and distinct characteristics of the new *Physocarpus*.

The photographs in FIG. 1 and FIG. 2 were taken of a 2-year-old plant as grown outdoors in two-gallon containers in Portage la Prairie, Manitoba, Canada.

Figure 1:
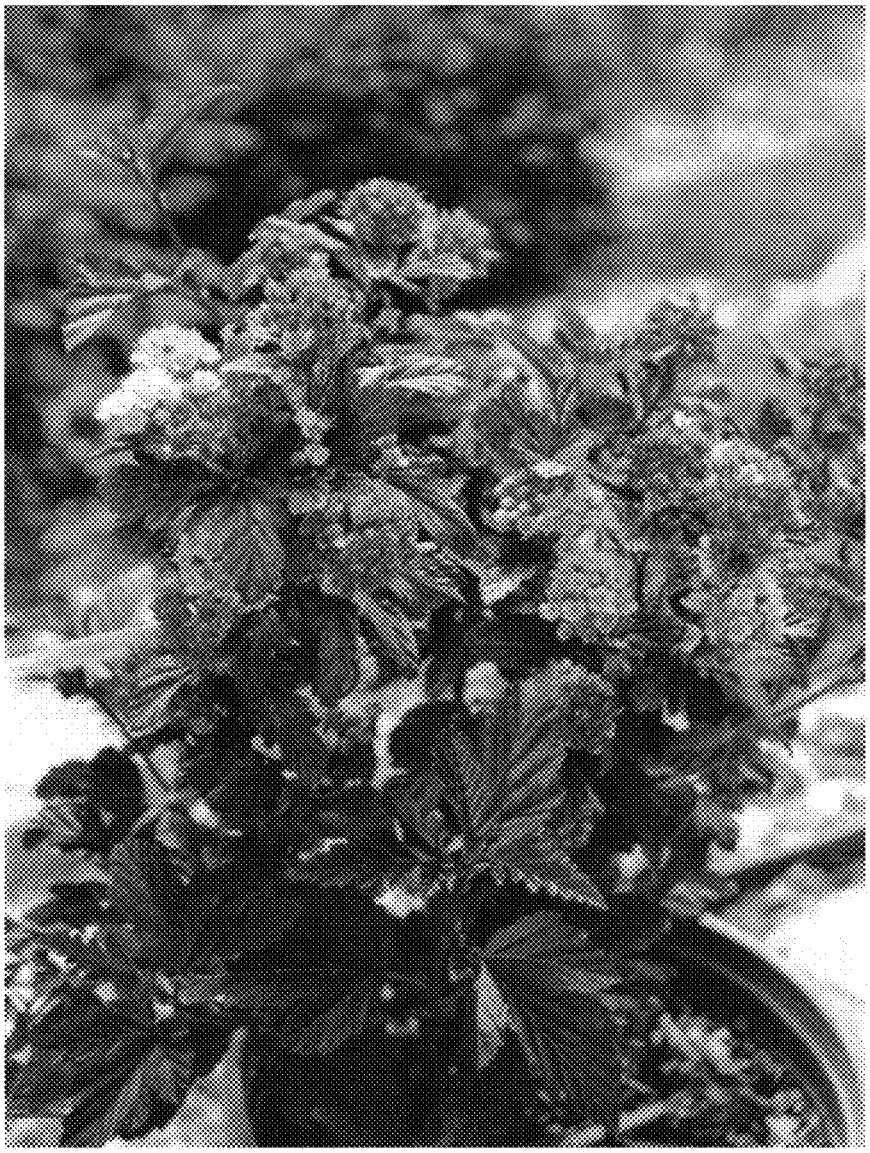

The photograph in FIG. 1 was provides a side view of 'Jefroy' in bloom.

Figure 2:
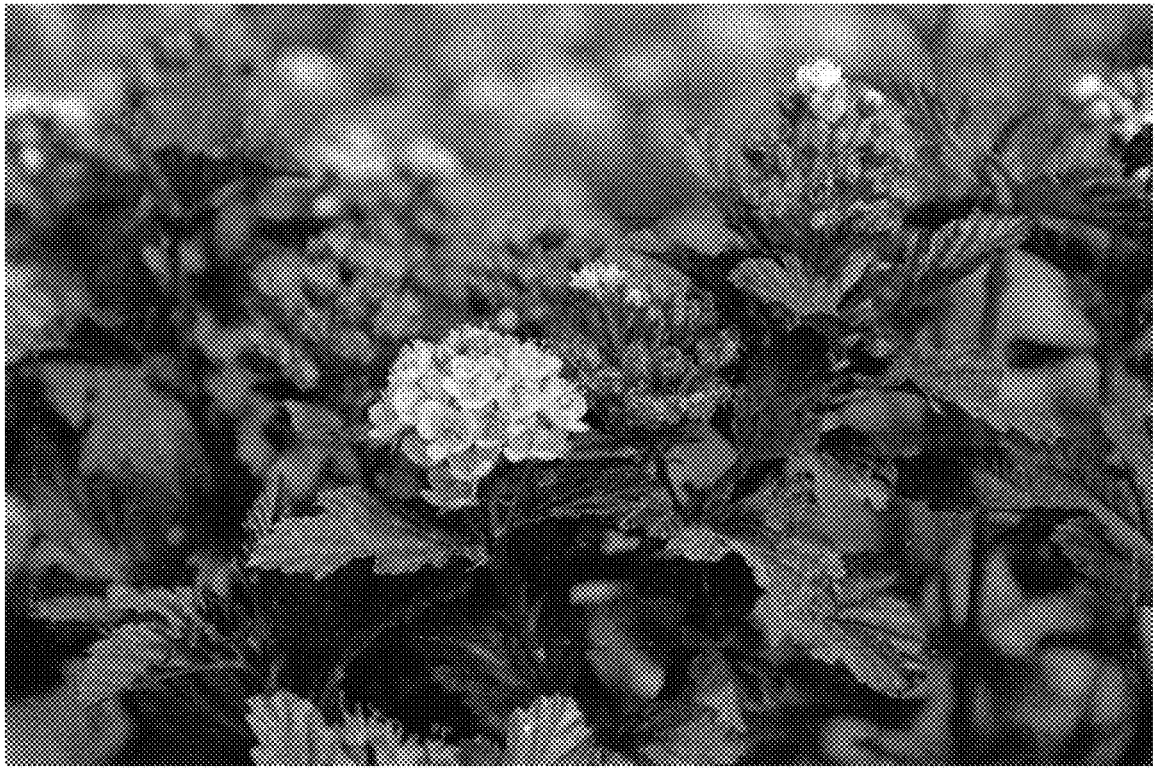

The photograph in FIG. 2 provides a close-up view of the flowers of 'Jefroy'.

Figure 3:
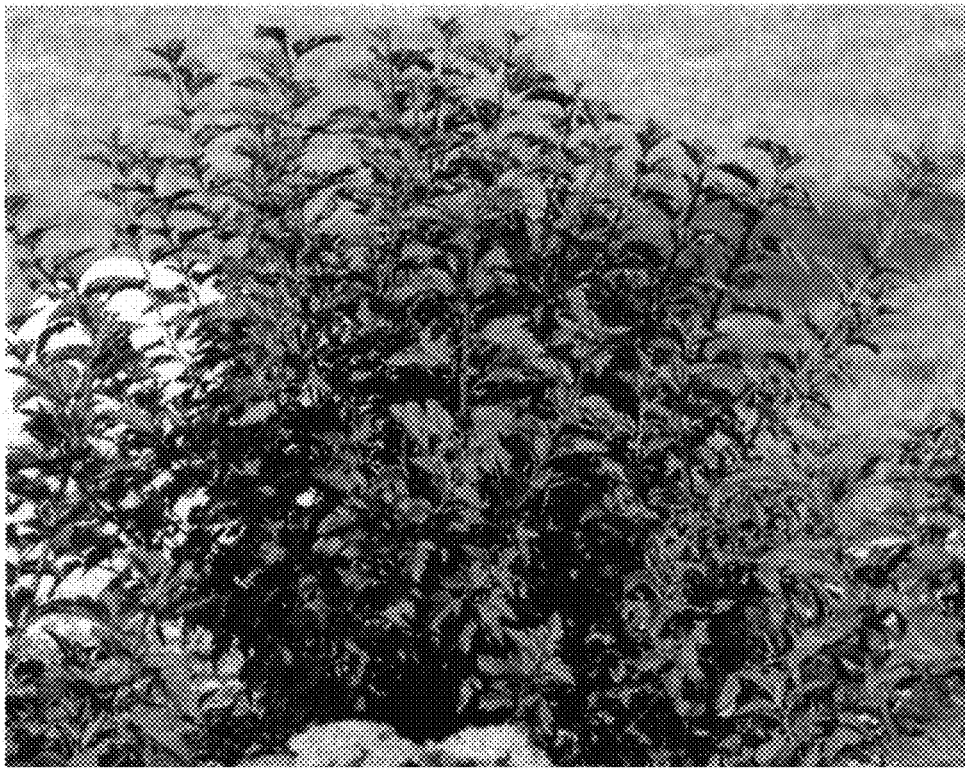

The photograph in FIG. 3 was taken of a 4-year-old plant as grown outdoors in a trial bed in Portage la Prairie, Manitoba, Canada.

The colors in the photographs are as close as possible with the digital photography and printing techniques utilized and the color codes in the detailed botanical description accurately describe the colors of the new *Physocarpus*.

BOTANICAL DESCRIPTION OF THE PLANT

The following is a detailed description of four-year-old plants of the new cultivar as grown in a trial bed in Portage la Prairie, Manitoba, Canada. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—About ten days in late June in southern Manitoba.

*Plant habit.*—Deciduous shrub.

*Plant habit.*—Compact and dwarf.

*Height and spread.*—An average of 1.25 m in height and spread as a mature plant in the landscape.

*Cold hardiness.*—At least in U.S.D.A. Zone 2.

*Diseases.*—Good disease resistance has been observed to powdery mildew caused by *Podosphaera aphanis* var. *physocarpi*.

*Growth rate.*—Moderate.

*Root development.*—Roots initiate in about 2 to 3 weeks and will fully root as a young plant in 2 to 3 months.

Branch description:

*Branch color.*—Young stems; between N186A and N186B, mature bark; a range of 200A, 200C with inner bark (stripes 3 mm in size) a color between N170B and 200D.

*Branch shape.*—Rounded to quadrangular.

*Branch size.*—Main branches; up to 60 cm in length, 1.5 cm in diameter, lateral branches; up to 35 cm in length, 8 mm in diameter, tertiary branches; average of 8 cm in length and 4 mm in diameter.

*Branch surface.*—New growth; glossy and very sparsely pubescent, mature bark; smooth, slightly ridged and matte, old twigs; splitting along ridges.

*Branching.*—Medium branched, main branches; an average of 11, strong, lateral branches; an average of 15, strong, tertiary branches; an average of 6 per lateral branch, moderately strong.

Foliage description:

*Leaf shape.*—Cordate to ovate.

*Leaf division.*—Simple.

*Leaf base.*—Rounded.

*Leaf apex.*—Acute to obtuse.

*Leaf venation.*—Palmate, upper surface; 161A, lower surface; 161B and sometimes flushed with 184A.

*Leaf margin.*—3-lobed with lobes crenate.

*Leaf attachment.*—Petiolate.

*Leaf arrangement.*—Alternate.

*Leaf surface.*—Upper surface is matte, lower surface is matte, both surfaces are crinkly.

*Leaf size.*—An average of 6 cm in length and 3.5 cm in width.

*Leaf number.*—Average of 32 per lateral branch 45 cm in length.

*Internode length.*—An average of 2 cm.

*Leaf color.*—Young leaves upper surface; very base 178A, blending up and turning 183A, tips are N187A, young leaves lower surface; a blend of 179A and 179D, mature and fall leaves upper surface; 186B, mature and fall leaves lower surface; a blend of 186C and 187A.

*Petioles.*—1.5 to 2 cm in length, 2 mm in diameter, matches stem color, medium strength, glossy and very sparsely pubescent surface.

*Stipules.*—2 at the base of each leaf, 7 mm in length, 2 mm in width, matches leaf color.

Flower description:

*Inflorescence size.*—Average of 5 cm in diameter and 4 cm in height.

*Inflorescence type.*—Small rotate flowers arranged in spherical corymb, similar to parents and typical of the species *Physocarpus opulifolius*.

*Inflorescence lastingness.*—Corymb lasts about 2 weeks, not persistent, individual flowers about 3 days.

*Flower quantity.*—About 44 flowers per corymb.

*Flower size.*—About 5 mm in depth, 1 cm in diameter.

*Flower form.*—Rotate.

*Flower fragrance.*—Very lightly sweet.

*Flower bud description.*—Elliptic to round in shape, average of 4 mm in length and 4 mm in diameter, a blend of 184A and 183D in color.

*Peduncles.*—Average of 1 cm in length and 3 mm in diameter, 178B with a flush of 178D, glabrous surface.

*Pedicels.*—Average of 7 mm in length and 1 mm in diameter, 42A, glabrous surface.

*Petal description.*—5, broadly obtuse in shape, margin is entire, lower and upper surface is glabrous, apex is obtuse, base is obtuse.

*Petal size.*—About 4 mm in length, 4 mm in width.

*Petal color.*—When opening and fully open upper and lower surface; a blend of N155B and 50D.

*Calyx size.*—Average of 3 mm in diameter, glabrous surface, inner surface color is 55B, outer surface color is mostly 53A with a light flush of 53B.

*Sepal description.*—5, subulate in shape, margin is entire, apex is acute, base cuneate-truncate, surface is glabrous, an average of 3 mm in length and 2 mm in width, a blend of 1A and 53A and 53B in color.

Reproductive organs:

*Gynoecium.*—Pistil; 4, average of 4 mm in length, stigma; 0.5 mm in diameter, round and flattened in shape and 18A in color, style; 3.5 mm in length and 18A in color, ovary; 4, oblong in shape, 1 mm in length, 0.5 mm in diameter, superior, 18A in color.

*Androecium.*—Stamens; an average of 29, 5 mm in length, anthers; oblong to rounded in shape, 0.5 mm in diameter, 187A in color, filaments; 4.5 mm in length, 18A in color, pollen observed.

*Fruit and seed.*—Fruit a firm-walled inflated follicle, splitting open at both seams, ovoid in shape, seeds; 2 to 4 seeds are hard, shiny, ovoid in shape, N45C in color at petal drop, 201A in color at maturity.

It is claimed:

1. A new and distinct cultivar of *Physocarpus* plant named 'Jefroy' substantially as herein illustrated and described.

* * * * *